United States Patent
Boone et al.

(10) Patent No.: US 10,295,535 B2
(45) Date of Patent: *May 21, 2019

(54) CLOSTRIDIUM DIFFICILE DEHYDROGENASE AND TOXIN AS A BIOMARKER FOR MONITORING INFECTION IN PATIENTS WITH CLOSTRIDIUM DIFFICILE DISEASE AND DIFFERENTIATING CARRIER STATE FROM ACTIVE DISEASE

(71) Applicant: TECHLAB, INC., Blacksburg, VA (US)

(72) Inventors: James Hunter Boone, Christianburg, VA (US); David M. Lyerly, Radford, VA (US); Robert J. Carman, Christiansburg, VA (US)

(73) Assignee: TECHLAB, INC., Blackburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/664,383

(22) Filed: Oct. 30, 2012

(65) Prior Publication Data

US 2013/0052640 A1    Feb. 28, 2013

Related U.S. Application Data

(63) Continuation-in-part of application No. 13/457,049, filed on Apr. 26, 2012.

(60) Provisional application No. 61/480,616, filed on Apr. 29, 2011.

(51) Int. Cl.
| | |
|---|---|
| *G01N 33/68* | (2006.01) |
| *G01N 33/569* | (2006.01) |
| *G01N 33/573* | (2006.01) |

(52) U.S. Cl.
CPC ..... *G01N 33/56911* (2013.01); *G01N 33/573* (2013.01); *G01N 33/6893* (2013.01); *G01N 2333/33* (2013.01); *G01N 2333/79* (2013.01); *G01N 2333/90611* (2013.01); *G01N 2333/90616* (2013.01); *G01N 2800/52* (2013.01); *G01N 2800/56* (2013.01)

(58) Field of Classification Search
CPC ........... G01N 33/56911; G01N 33/573; G01N 33/6893; G01N 2333/33; G01N 2333/79; G01N 2333/90616; G01N 2800/52; G01N 2800/56; G01N 2333/90611
See application file for complete search history.

(56) References Cited

U.S. PATENT DOCUMENTS

| | | | |
|---|---|---|---|
| 7,192,724 B2 | 3/2007 | Boone et al. | |
| 8,343,726 B2 * | 1/2013 | Boone et al. | 435/7.1 |
| 2003/0157113 A1 | 8/2003 | Terman | |
| 2008/0096189 A1 | 4/2008 | Boone et al. | |
| 2009/0203021 A1 | 8/2009 | Cockerill, III et al. | |
| 2009/0253155 A1 | 10/2009 | Boone et al. | |
| 2011/0296544 A1 | 12/2011 | Domon et al. | |
| 2012/0276059 A1 | 11/2012 | Boone et al. | |
| 2016/0370361 A1 | 12/2016 | Boone et al. | |

FOREIGN PATENT DOCUMENTS

| | | |
|---|---|---|
| JP | 2000155121 A | 6/2000 |
| JP | 2008522165 A | 6/2008 |
| JP | 2014519018 A | 8/2014 |
| WO | 9845706 A1 | 10/1998 |
| WO | 0239883 A2 | 5/2002 |
| WO | 2009108652 A1 | 9/2009 |
| WO | 201214935 A1 | 11/2012 |

OTHER PUBLICATIONS

Reller ME et al. (2007). Yield of stool culture with isolate toxin testing versus a two-step algorithm inclduing stool toxin testing for detection of toxigenic Clostridium difficile. Journal of Clinical Microbiology, v45(11), p. 3601-3605.*
Steiner TS et al. (1997). Fecal Lactoferrin, Interleukin-1beta, and Interleukin-8 are elevated in patients with severe Clostridum difficile colitis. Clinical and Diagnostic Laboratory Immunology, v4(6), p. 719-722.*
Eastwood et al. (2009). Comparison of Nine Commercially Available Clostridium difficile Toxin Detection Assays, a Real-Time PCR Assay for C. difficile tcdB, and a Glutamate Dehydrogenase Detection Assay to Cytotoxin Testing and Cytotoxigenic Culture Methods. Journal of Clinical Microbiology, v47(10), p. 3211-3217.*
Vaughn et al. (2006). C. DiffChek™—60: A Rapid and Cost Effective Method for Detection of Clostridium difficile in Fecal Specimens. Poster from the Clinical Virology meeting. Pub. Date from http://www.techlab.com/diagnostics/c-difficile/c-diff-chek-60-t5025/.*
Kelly (1994). Clostridium Difficile Colitis. The New England Journal of Medicine, v330(4), p. 257-262.*

(Continued)

*Primary Examiner* — Sean C. Barron
(74) *Attorney, Agent, or Firm* — Shook, Hardy & Bacon L.L.P.

(57) ABSTRACT

*Clostridium difficile* disease involves a range of clinical presentations ranging from carrier status with other causes of symptoms to mild and self-limiting diarrhea to life-threatening pseudomembranous colitis and megacolon. Cases of *C. difficile* are treated differently depending on the presence and then the severity of disease. Patients that are carriers may not receive treatment with concern of causing the disease. Mild to moderate cases may be treated with metronidazole while severe and relapsing cases are often treated with vancomycin or fidaxomicin. Current molecular assays are highly sensitive for detecting toxigenic *C. difficile* and cannot rule out carrier status. Utilization of a biomarker panel that includes *C. difficile* antigen (GDH), toxins A and B, and fecal lactoferrin allows clinicians to differentiate between a carrier state and active state of *C. difficile* and allows for monitoring to evaluate the effectiveness of treatment.

12 Claims, 6 Drawing Sheets

(56) References Cited

OTHER PUBLICATIONS

C. Diff CHEK™—60 product insert (2013), from Techlab. Pub. Date from http://www.techlab.com/diagnostics/c-difficile/c-diff-chek-60-t5025/.*
van Langerberg (2009). The potential value of faecal lactoferrin as a screening test in hospitalized patients with diarrhoea. Internal Medicine Journal, v40(12), p. 819-827.*
Tanous et al. Applied and Environmental Microbiology, Feb. 2006, v72(2), p. 1402-1409Glutamate Dehydrogenase Activity Can Be Transmitted Naturally to Lactococcus lactis Strains to Stimulate Amino Acid Conversion to Aroma Compounds. (Year: 2006).*
First Action Interview Office Action in U.S. Appl. No. 13/457,049 dated Sep. 26, 2013, 33 pages.
Non-Final Office Action in U.S. Appl. No. 13/457,064, dated Jun. 27, 2013, 19 pages.
European Extended Search Report dated Oct. 15, 2014 in Application No. 12777788.6, 9 pages.
Shen, E.P. et al, Current treatment options for severe Clostridium difficile-associated disease, Gastroenterology & Hepatology, Millennium Medical Publishing, US, vol. 4, No. 2, Feb. 1, 2008, pp. 134-139, XP009148951.
PCT Search Report and Written Opinion re PCT/US12/35495, dated Jul. 27, 2012, 34 pages.
Oppenheim, Scientific Symposium on New Approaches to Clostridium Difficle Testing [online] Oct. 23, 2010 [retrieved Jul. 6, 2012]. Available on the internet: <URL: http://www.alere.co.uk/pdf/150411101655-Alere_Barcelona_FINAL1.pdf>. Especially p. 2 col. 2 para 2-4, p. 2 table 2, p. 3 col. 1 para 1-3 and col. 2 para 1.
New York-Presbyterian. Guidelines for the Management of Clostridium difficile-Associated Disease (CDAD) in Adult Patients [online] Aug. 28, 2008 {retrieve on Jul. 6, 2012]. Available on the internet: <URL:http://www.id.hs.columbia.edu/documents/Guidelines-Clostridiumdifficile-8-28.08.pdf>. Especially p. 1 para 2, p. 2 table.
Shastri et al. Prospective multicenter study evaluating fecal calprotectin in adult acute bacterial diarrhea. Am J Med Dec. 2008 vol. 121 No. 12 pp. 1099-1106. Especially abstract.
Yoon et al. Treatment of Refractory/Recurrent C. difficile-associated Disease by Donated Stool Transplanted Via Colonscopy. J Clin Gastroenterol Sep. 2010 vol. 44 No. 8 pp. 562-566. Especially abstract.
PCT Search Report and Written Opinion re PCT/US12/35495, dated Mar. 12, 2013, 21 pages.
Kvach et al. "Comparison of BD GeneOhm Cdiff Real-Time PCR Assay with a Two-Step Algorithm and a Toxin A/B Enzyme-Linked Immunosorbent Assay for Diagnosis of Toxigenic Clostridium difficile infection." Journal of Clinical Microbiology (online), Jan. 2010 [Retrieved on Feb. 2012-2013], vol. 48, No. 1, para 1-3, p. 110, col. 2, para 2-3; pp. 111, col. 1, para 3; p. 112, col. 1, para 3; p. 112, col. 1, para 3.
Preinterview First Action Interview dated Mar. 22, 2013 in U.S. Appl. No. 13/457,064; 27 pages. No references cited.
Preinterview First Action Interview dated Apr. 10, 2013 in U.S. Appl. No. 13/457,049; 44 pages.
Kelley CP et al. (1994). Clostridium difficile colitis. New England Journal of Medicine, v330(4), p. 257-262.
van Langerberg DR et al. (avail online Oct. 22, 2009). The potential value of faecal lactoferrin as a screening test in hospitalized patients with diarrhoea. Internal Medicine Journal, v40(12), p. 819-827.
Aas J et al. (2003). Recurrent Clostridium difficile colitis: Case series involving 18 patients treated with donor stool administered via a nsaogastic tube. Clinical Infectious Dieases, v36, p. 580-585.
Dai et al., Scandinavian Journal of Gastroneterology, 42: 1440-1444, 2007.
Reller ME et al. (2007). Yield of stool culture with isolate toxin testing versus a two-step algorithm including stool toxin testing for detection of toxigenic Clostridium difficile. Journal of Clinical Microbiology, v 45 (11), p. 3601-3605.

Limburg PJ et al (2000). Fecal Calprotectin Levels Predict Colorectal Inflammation Among Patients with Chronic Diarrhea Referred for Colonoscopy. The American Journal of Gastroenterology, v95(10), p. 2831-2837.
Issa M. et al. (2000). Clostridium difficile and Inflammatory Bowel Disease. Inflammatory Bowel Diseases, v14(10), p. 1432-1442.
Barlett, J., Taylor, S., Chang, T. and J. Dzink. 1980. Clinical and laboratory observations in Clostridium difficile colitis. Amer. J. of Clin. Nutri. 33:2521-2526.
Barlett, J., and D. Gerding. 2008. Clinical recognition and diagnosis of Clostridium difficile infection. Clinical Infectious Disease 46:S12-8.
Belmares, J., Gerding, D., Parada, J., Miskevics, S., Weaver, F. and S. Johnson. 2007. Outcome of metronidazole therapy for Clostridium difficile disease and correlation with a scoring system. J. of Infection. 55:495-501.
Belmares, J., Gerding, D., Tillotson, G. and S. Johnson. 2008. Measuring the severity of Clostridium difficile infection: implications for management and drug development. Expert Rev. Anti Infect. Ther. 6(6)897-908.
Bhangu, A., Czapran, A., Bhangu, S. and D. Pillay. 2010. Optimum timing of blood tests for monitoring patients with Clostridium difficile-Associated diarrhea. J. Investigative Medicine. 58(4):621-624.
Henrich, T., Krakower, D., Bitton, A., and D. Yokoe. 2009. Clinical risk factors for severe Clostridium difficile-associated disease. Emerging Infectious Disease 15:415-422.
Inca, R., Dal Pont, E., Di Leo, V., Ferronato, A., Fries, W., Vettorato, M., Marlines, D. and G. Sturniolo. 2006. Calprotectin and lactoferrin in the assessment of intestinal inflammation and organic disease. Int. J. Colorectal. Dis. ?.
Kane, S., Sandborn, W., Rufo, P., Zholudev, A, Boone, J., Lyerly, D., Camilleri, M., and S. Hanauer. 2003. Fecal lactoferrin is a sensitive and specific marker in identifying intestinal inflammation. Am. J. Gastroenterol. 98:1309-1314.
Kayazawa, M., Saitoh, O., Kojima, K., Nakagawa, K., Tanaka, S., Tabata, K., Matsuse, R., Uchida, K, Hoshimoto, M., Hirata, I. and K. Katsu. 2002. Lactoferrin in whole gut lavage fluid as a marker for disease activity in inflammatory bowel disease: Comparison with other neutrophil-derived proteins. Amer. J. of Gastroenterol. 97(2):360-369.
Kim, H., Rhee, S., Pothoulakis, C. and J. Lamont. 2007. Inflammation and Apoptosis in Clostridium difficile enteritis is mediated by PGE2 Up-Regulation of Fas Ligand. Gastroenterology. 133:875-886.
Kyne, L., Merry, C., O'Connel, B., Kelly, A., Keane, C., and D. O'Neill. 1999. Factors associated with prolonged symptoms and severe disease due to Clostridium difficile. Age and Ageing 28:107-113.
Lamb, C., Mohiuddin, M., Gicquel, J., Neely, D., Bergin, F., Hanson, J., and J. Mansfield. 2009. Faecal calprotectin or lactoferrin can identify postoperative recurrence in Crohn's disease. Br. J. Surg. 96(6):663-674.
Limaye, A., Turgeon, D., Cookson, B. and T. Fritsche. 2000. Pseudomembranous colitis caused by a toxin A− B+ Strain of Clostridium difficile. J of Clin. Microbiol. 38(4):1696-1697.
Linevsky, J., Pothoulakis, C., Keates, M., Warny, M., Keates, A., Lamont, T. and C. Kelly. 1997. IL-8 release and neutrophil activation by Clostridium difficile toxin-exposed human monocytes. Amer. Physiological Society. 1333-1340.
McFarland, L. 2005. Alternative treatments for Clostridium difficile disease:what really works. J. Med. Microbiol. 54:101-111.
Merrigan, M., Venugopal, A., Mallozzi, M., Roxas, B., Viswanathan, V., Johnson, S., Gerding, D. and G. Vedantam. 2010. Human hypervirulent Clostridium difficile strains exhibit increased sporulation as well as robust toxin production. J. of Bacteriology. 192(19):4904-4911.
Morgan, O., Rodrigues, B., Elston, T., Verlander, N., Brown, D., Brazier, J., and M. Reacher. 2008. Clinical severity of Clostridium difficile PCR ribotype 027: A case-case study. PloS ONE 3(3):1-6.

(56) References Cited

OTHER PUBLICATIONS

Musher, D., Aslam, S., Logan, N., Nallacheru, S., Bhaili, I., Borchert, F., and R. Hamill. 2005. Relatively Poor Outcome after Treatment of Clostridium difficile Colitis with Metronidazole. Clin. Infect. Diseases. 40:1586-1590.
Pant, C., Madonia, P., Minocha, A., Manas, K., Jordan, P., and P. Bass. 2009. Laboratory markers as predictors of mortality in patients with Clostridium difficile infection. Journal of Investigative Medicine 57:1-3.
Pepin, J., Valiquette, L, Alary, M., Villemure, P., Pelletier, A., Forget, K., and D. Chouinard. 2004. Clostridium difficile-associated diarrhea in a region of Quebec from 1991 to 2003: a changing pattern of disease severity. CMAJ 171:466-472.
Pothoulakis, C., Sullivan, R., Melnick, D., Triadafilopoulos, G., Gadenne, A., Meshulam, T. and T. Lamont. 1988. Clostridium difficile toxin A stimulates intracellular calcium release and chemotactic response in human granulocytes. J. Clin. Invest. 81:1741-1745.
Rocha, M., Maia, M., Bezerra, L., Lyerly, D., Guerrant, R., Ribeiro, R., and A. Lima. 1997. Clostridium difficile toxin A induces the release of neutrophil chemotactic factors from rat peritoneal macrophages: Role of interleukin-1beta, tumor necrosis factor alpha, and leukotrienes. Infection and Immunity. 65(7):2740-2746.
Schleupner, M., Garner, D., Sosnowski, K., Schleupner, C., Barrett, L., Hirsch, D., and R. Guerrant. 1995. Concurrence of Clostridium difficile toxin A enzyme-linked immunosorbent assay, fecal lactoferrin assay, and clinical criteria with C. difficile cytotoxin titer in two patient cohorts. J. of Clin. Microbiol. 33(7):1755-1759.
Sidhu, R., Wilson, P., Wright, A., Yau, C., Cruz, F., Foye, L., Morley, S., Lobo, A., Mcalindon, M. and S. Sanders. 2010. Faecal lactoferrin—a novel test to differentiate between the irritable and inflamed bowel. Aliment Pharmacol Ther. 31:1365-1370.
Sipponen, T., Savilahti, E., Kolho, K., Nuutinen, H., Turunen, U., and M. Farkkila. 2008. Crohn's disease activity assessed by Fecal Calprotectin and Lactoferrin: Correlation with Crohn's disease activity index and endoscopic findings. Inflamm. Bowel. Dis. 14(1):40-46.
Sunenshine, R. and L. McDonald. 2006. Clostridium difficile-associated disease: New Challenges from an established pathogen. Cleveland Clinic Journal of Medicine. 73(2)187-197.
Vieira, A., Fang, C., Rolim, E., Klug, W., Steinwurz, F, Giovanni, L., Rossini, B., and P. Candelaria. 2009. Inflammatory bowel disease activity assessed by fecal calprotectin and lactoferrin: correlation with laboratory parameters, clinical, endoscopic and histological indexes. BMC Research Notes. 2(221):1-7.
Walker, T., Land, M., Kartashov, A., Saslowsky, T., Lyerly, D., Boone, J. and P. Rufo. 2007. Fecal lactoferrin is a sensitive and specific marker of disease activity in children and young adults with inflammatory bowel disease. J. Pediatric Gastroenterol. Nutr. 44(4):414-422.
Wilcox, M. 2010. New clinical practice guidelines for Clostridium difficile infection. Infectious Diseases in Clinical Practice. 18(5):329-331.
Final Office Action dated Apr. 30, 2014 re U.S. Appl. No. 13/457,049, 42 pages.
Non-Final Office Action dated May 4, 2015 in U.S. Appl. No. 13/457,049, 36 pages.
IBD-Scan product insert, by TechLab. 36 pages. Apr. 2008.
Wren et al. (2009a). Laboratory diagnosis of Clostridium difficile infection. An evaluation of tests for faecal toxin, glutamate dehydrogenase, lactoferrin and toxigenic culture in the diagnostic laboratory. British Journal of Biomedical Science. v66(1), p. 1-5.
Wren et al. (2009b).Detection of. Clostridium difficile infection: a suggested laboratory diagnostic algorithm. British Journal of Biomedical Science, v66(4), p. 175-179.
Non-Final Office Action dated Sep. 28, 2016 in U.S. Appl. No. 13/457,049, 27 pages.
Canadian Office Action dated Jul. 13, 2016 for Canadian Patent Application No. 2871613, 4 Pages.
European Extended Search Report dated Oct. 9, 2015 in Application No. 12838635.6, 12 pages.
L. Fenner et al: "Rapid and Reliable Diagnostic Algorithm for Detection of Clostridium difficile", Journal of Clinical Microbiology, vol. 46, No. 1, Nov. 21, 2007 (Nov. 21, 2007 ), pp. 328-330, XP055216114, ISSN: 0095-1137, DOI: 10.1128/JCM.01503-07.
Oppenheim et al: "Scientific Symposium on New Approaches to Clostridium difficile Testing Conference report from the Satellite Symposium held during the 2010 United European Gastroenterology Week (UEGW) Chairwoman", Oct. 23, 2010 (Oct. 23, 2010), XP0550931 04, Retrieved from the Internet: URL:http://www.medica-tec.com/chilfiles/Simposio Alere en Barcelona Clostridium Diff .pdf [retrieved on Dec. 12, 2013].
First Examination Report dated Sep. 9, 2015 in New Zealand Application No. 701004, 3 pages.
Final Office Action dated Nov. 2, 2015 in U.S. Appl. No. 13/457,049, 22 pages.
First Action Interview Preinterview Communication dated Feb. 25, 2015 in U.S. Appl. No. 14/249,814, 7 pages.
Michael T. Kelly, Commercial Latex Agglutination Test for Detection of Clostridium Difficile-Associated Diarrhea, Journal of Clinical Microbiology, 1987, vol. 25, No. 7, pp. 1244-1247.
David M. Lyerly, Identification of the Latex Test-Reactive Protein of Clostridium Difficile As Glutamate Dehydrogenase, Journal of Clinical Microbiology, 1991, vol. 29, No. 11, pp. 2639-2642.
David M. Lyerly, Commercial Latex Test for Clostridium Difficile Toxin A Does Not Detect Toxin A, Journal of Clinical Microbiology, 1986, vol. 23, No. 3, pp. 622-623.
New Zealand Examination Report dated Apr. 4, 2016 in Application No. 701004, 5 pages.
Final Office Action dated Feb. 9, 2017 in U.S. Appl. No. 14/249,814, 24 pages.
Translated Japanese Office Action dated Jan. 4, 2017 in Japanese Patent Application No. 2015-508933, 4 pages.
New Clinical Examinations—Infectious diseases (Intestinal infectious diseases)-Clostridium difficile antigen (toxin), Hiroko Nigorigawa, in Shindan to Chiryo (Diagnosis and Treatment), 2009, vol. 97, No. 9, pp. 1740-1742.
Shetty N, The Role of Glutamate Dehydrogenase for the Detection of Clostridium Difficile in Faecal Samples: A Meta-Analysis, J Hosp Infect, 2011, vol. 47, NR: 10, pp. 3211-3217.
Kelly W F, Evaluation of the latex agglutination test for detection of Clostridium difficile, Archives of pathology & laboratory medicine, 1992,vol. 116, No. 5, p. 517-520.
C. Diff Check-60 T5025, An enzyme immunoassay for the detection of glutamate dehydrogenase (GDH) produced by both toxigenic and non-toxigenic strains of Clostridium difficile, Dec. 16, 2016, URL,http://www.techlab.com/diagnostics/c-difficile/c-diff-chek-60-t5025.
Office Action dated Apr. 7, 2017 in European Patent Application No. 12838635.6, 8 pages.
Canadian Office Action dated Apr. 18, 2017 for Canadian Patent Application No. 2,871,613, 4 pages.
Australian Office Action and Examination Report in Application No. 2012318345 dated Dec. 12, 2017, 3 pages.
Non-Final Office Action in U.S. Appl. No. 14/249,814 dated Dec. 15, 2017, 18 pages.

\* cited by examiner

| PATIENT CHARACTERISTICS | | PERCENT OF TOTAL N=39 | PERCENT OF MOD-TO-SEVERE N=15 | PERCENT OF MODERATE N=21 | PERCENT OF MILD N=3 |
|---|---|---|---|---|---|
| GENDER | MALE | 41 | 60 | 29 | 33 |
| | FEMALE | 59 | 40 | 71 | 67 |
| AGE | < 65 YR | 44 | 40 | 48 | 33 |
| | > 64 YR | 56 | 60 | 52 | 67 |
| PAIN | YES | 67 | 60 | 71 | 67 |
| | NO | 33 | 40 | 29 | 33 |
| CO-MORBIDITIES | DIABETES | 30 | 13 | 29 | 33 |
| | CANCER | 23 | 13 | 29 | 33 |
| | RENAL FAILURE | 23 | 20 | 29 | 33 |
| | PNEUMONIA | 18 | 27 | 10 | 0 |
| STOOL CONSISTENCY | SOLID | 3 | 0 | 5 | 0 |
| | SEMI-SOLID | 44 | 33 | 43 | 100 |
| | LIQUID | 54 | 67 | 52 | 0 |
| CLINICAL ASSESSMENT | SEVERE | 38 | 100 | 0 | 0 |
| | MODERATE | 54 | 0 | 100 | 0 |
| | MILD | 8 | 0 | 0 | 100 |

FIG. 4A

| N=9 ID | AGE (YR) | SEX M/F | T=0 LAC (μg/g) | GDH | ABII | SPORE COUNTS | PCR RIBOTYPE | FIRST FOLLOW-UP LAC (μg/g) | GDH | ABII | SPORE COUNTS | PCR RIBOTYPE |
|---|---|---|---|---|---|---|---|---|---|---|---|---|
| 3 | 76 | F | 448 | 4.144 | 3.986 | 1.80E+04 | ARL 251 | 0 | 0 | 0 | 0 | N/A |
| 4 | 78 | M | 44 | 4.342 | 4.126 | 5.00E+04 | ARL 305 | 22 | 0 | 0 | 0 | N/A |
| 5 | 65 | F | 13 | 4.197 | 4.054 | 4.00E+05 | ARL 005 | 18 | 0 | 0 | 0 | N/A |
| 7 | 53 | M | 406 | 4.307 | 3.938 | 1.60E+04 | ARL 027 | 0 | 0 | 0 | 0 | N/A |
| 11 | 24 | F | 151 | 4.101 | 0.556 | 7.00E+02 | ARL 001 | 1 | 0 | 0 | 0 | N/A |
| 12 | 55 | M | 14 | 4.487 | 1.787 | 4.00E+02 | ARL 027 | 12 | 0 | 0 | 0 | N/A |
| 14 | 79 | F | 515 | 4.327 | 3.889 | 3.50E+05 | ARL 054 | 4 | 0 | 0 | 0 | N/A |
| 17 | 77 | F | 1291 | 4.304 | 4.215 | 8.00E+03 | ARL 059 | 2 | 0 | 0 | 0 | N/A |
| 19 | 72 | F | 1826 | 4.125 | 4.110 | 4.50E+05 | ARL 027 | 72 | 0.098 | 0 | 0 | N/A |
| MEDIAN | 72 | | 406 | 4.304 | 3.986 | 1.80E+04 | 33% 027 | 4 | 0 | 0 | 0 | N/A |

FIG. 4B

| N=5 ID | AGE (YR) | SEX M/F | T=0 LAC (μg/g) | GDH | ABII | SPORE COUNTS | PCR RIBOTYPE | FIRST FOLLOW-UP LAC (μg/g) | GDH | ABII | SPORE COUNTS | PCR RIBOTYPE |
|---|---|---|---|---|---|---|---|---|---|---|---|---|
| 2 | 80 | F | 73 | 4.180 | 3.130 | 3.20E+03 | ARL 027 | 17 | 5.000 | 0.478 | 4.00E+03 | ARL 027 |
| 8 | 35 | M | 403 | 4.225 | 4.097 | 1.30E+05 | ARL 027 | 0 | 0.633 | 0.943 | 5.80E+03 | ARL 027 |
| 10 | 79 | F | 10 | 0.038 | 0 | 3.00E+04 | ARL 014 * | 2 | 0 | 0 | 1.00E+02 | ARL 027 |
| 15 | 82 | F | 85 | 4.434 | 3.696 | 5.00E+03 | ARL 126 | 57 | 0 | 0 | 1.00E+02 | ARL 126 |
| 16 | 49 | F | 164 | 5 | 1.512 | 1.90E+05 | ARL 056 | 0.4 | 4.151 | 0 | 4.20E+04 | ARL 379 |
| MEDIAN | 79 | | 85 | 4.225 | 3.130 | 3.00E+04 | 40% 027 | 2 | 0.633 | 0 | 4.00E+03 | 60% 027 |

FIG. 4C

| N=4 ID | AGE (YR) | SEX M/F | T=0 LAC (μg/g) | GDH | ABII | SPORE COUNTS | PCR RIBOTYPE | FIRST FOLLOW-UP LAC (μg/g) | GDH | ABII | SPORE COUNTS | PCR RIBOTYPE |
|---|---|---|---|---|---|---|---|---|---|---|---|---|
| 1 | 59 | F | 11 | 4.192 | 0.884 | 6.20E+04 | ARL 054 | 433 | 3.89 | 1.442 | 1.00E+05 | ARL 103 |
| 18 | 75 | M | 423 | 5.000 | 4.293 | 1.50E+05 | ARL 126 | 196 | 3.977 | 0.798 | 4.40E+04 | ARL 126 |
| 9 | 75 | F | 301 | 4.225 | 4.076 | 1.50E+05 | ARL 005 | 135 | 4.153 | 3.691 | 2.80E+04 | ARL 027 |
| 20 | 86 | F | 1541 | 4.503 | 2.299 | 1.00E+04 | ARL 126 ** | 2155 | 4.157 | 3.909 | 2.80E+04 | ARL 126 |
| MEDIAN | 75 | | 362 | 4.364 | 3.188 | 1.06E+05 | NO 027 | 315 | 4.065 | 2.567 | 3.60E+04 | 25% 027 |

| TIME (DAYS) | GDH (ng/mL) | TOXIN ABII OD | LACTOFERRIN (ug/mL) |
|---|---|---|---|
| 1 | 1040 | 3.334 | 7 |
| 2 | 4100 | 3.574 | 11 |
| 3 | 2700 | 0.003 | 32 |
| 4 | 60 | 0.003 | 42 |
| 5 | 20 | 0.002 | 44 |
| 6 | 0 | 0.003 | 19 |
| 7 | 0 | 0.003 | 1 |
| 8 | 0 | 0.002 | 3 |
| 9 | 0 | 0.002 | 7 |
| 10 | 0 | 0.003 | 2 |

FIG. 7

| TIME (DAYS) | GDH (ng/mL) | TOXIN ABII OD | LACTOFERRIN (ug/mL) |
|---|---|---|---|
| 1 | 4050 | 0.091 | 33 |
| 3 | 1090 | 0.026 | 1 |
| 5 | 4040 | 0.209 | 3 |
| 7 | ND | 0.238 | 3 |
| 9 | 2220 | 0.377 | 1 |
| 11 | 4330 | 0.313 | 2 |
| 13 | 4220 | 0.454 | 4 |
| 15 | 7250 | 0.114 | 15 |

FIG. 8

| ID | AGE | SEX | TOXIQENIC CULTURE | LACTOFERRIN LEVEL ug/g | SYMPTOM | STOOLS/DAY | SERUM ALBUMIN | WBC | GDH ng/g | TOXIN TISSUE CULTURE | AB II | MOLECULAR ASSAY | PATIENT C.DIFFICILE STATUS |
|---|---|---|---|---|---|---|---|---|---|---|---|---|---|
| 1 | 69 | F | + | 152 | PAIN | 3 | 1.8 | 12.5 | 3447 | + | 3.960 | Pos | SUSPECT DISEASE |
| 2 | 59 | M | + | 132 | PAIN | 20 | 1.9 | 14 | 3137 | + | 3.960 | Pos | SUSPECT DISEASE |
| 3 | 56 | F | + | 6 | PAIN | 4 | 2.8 | 5.2 | 739 | - | 0.008 | Pos | SUSPECT CARRIER |
| 4 | 75 | M | + | 962 | NO PAIN | 8 | 2.1 | 9.1 | 6851 | + | 3.117 | Pos | SUSPECT DISEASE |
| 5 | 77 | F | + | 1391 | PAIN | 8 | 3.6 | 19.4 | ND | + | 3.725 | Pos | SUSPECT DISEASE |
| 6 | 83 | F | + | 210 | PAIN | 4 | 3.3 | 8 | 1571 | + | 3.844 | Pos | SUSPECT DISEASE |
| 7 | 67 | F | + | 38 | PAIN | 20 | 3.2 | 20.2 | ND | + | 0.066 | Pos | SUSPECT DISEASE |
| 8 | 30 | F | + | 4 | PAIN | 8 | ND | ND | 0 | - | 0.001 | Pos | SUSPECT CARRIER |
| 9 | 83 | M | + | 308 | PAIN | 3 | 1.8 | 25.8 | 206 | + | 0.010 | Pos | SUSPECT DISEASE |
| 10 | 77 | M | + | 623 | NO PAIN | 8 | 3.4 | 15.8 | 370 | + | 4.321 | Pos | SUSPECT DISEASE |
| 11 | 86 | M | + | 561 | NO PAIN | 10 | 2.7 | 28.6 | 186 | + | 3.985 | Pos | SUSPECT DISEASE |
| 12 | 66 | M | + | 771 | NO PAIN | 4 | ND | 16.6 | 14097 | + | 4.074 | Pos | SUSPECT DISEASE |
| 13 | 72 | F | + | 26 | NO PAIN | 8 | ND | 8 | 175 | - | 0.002 | Pos | SUSPECT CARRIER |
| 14 | 79 | M | + | 422 | PAIN | 4 | ND | 15.6 | 13282 | + | 2.028 | Pos | SUSPECT DISEASE |
| 15 | 84 | F | + | 648 | NO PAIN | 5 | 2 | 18.5 | 12052 | + | 4.192 | Pos | SUSPECT DISEASE |
| 16 | 77 | F | + | 10 | PAIN | 10 | 3.2 | 3.6 | 125 | - | 0.007 | Pos | SUSPECT CARRIER |
| 17 | 77 | F | + | 39 | NO PAIN | 8 | 3.4 | 14.4 | 7987 | + | 3.743 | Pos | SUSPECT DISEASE |
| 18 | 88 | F | + | 376 | NO PAIN | 6 | 2.6 | 21.3 | 747 | + | 3.927 | Pos | SUSPECT DISEASE |
| 19 | 83 | F | + | 6 | PAIN | 8 | ND | 8 | 123 | + | 0.105 | Pos | SUSPECT CARRIER |
| 20 | 67 | F | + | 704 | PAIN | 10 | 2.7 | 33.7 | 1048 | + | 4.152 | Pos | SUSPECT DISEASE |
| 21 | 68 | F | + | 57 | PAIN | 6 | 2.1 | 17.9 | 5733 | + | 4.055 | Pos | SUSPECT DISEASE |
| 22 | 88 | F | + | 5 | NO PAIN | 3 | 2.4 | 8 | ND | - | 0.051 | Pos | SUSPECT CARRIER |
| 23 | 68 | F | + | 376 | NO PAIN | 5 | ND | 14.2 | 0 | - | 0.066 | Pos | SUSPECT CARRIER |
| 24 | 76 | F | + | 94 | NO PAIN | 5 | 3.1 | 4.3 | 604 | + | 3.990 | Pos | SUSPECT DISEASE |

FIG. 9

CLOSTRIDIUM DIFFICILE DEHYDROGENASE AND TOXIN AS A BIOMARKER FOR MONITORING INFECTION IN PATIENTS WITH CLOSTRIDIUM DIFFICILE DISEASE AND DIFFERENTIATING CARRIER STATE FROM ACTIVE DISEASE

CROSS-REFERENCE TO RELATED APPLICATIONS

This application is a continuation-in-part application of U.S. Nonprovisional application Ser. No. 13/457,049, filed Apr. 26, 2012, entitled "Fecal Lactoferrin as a Biomarker for Determining Disease Severity and for Monitoring Infection in Patients with Clostridium Difficile Disease," which claims priority to U.S. Provisional Patent Application No. 61/480,616, filed Apr. 29, 2011, entitled "Fecal Lactoferrin as a Biomarker for Determining Disease Severity and for Monitoring Infection in Patients with Clostridium Difficile Disease," both of which are herein incorporated by reference in their entirety.

BACKGROUND

*Clostridium difficile* infection (CDI) involves a range of clinical presentations including mild to self-limiting diarrhea to life-threatening pseudomembranous colitis and megacolon. Many healthy persons (e.g., infants) carry *Clostridium difficile* (*C. difficile*), and many patients become asymptomatic carriers after admission to the hospital. Most cases are diagnosed based on clinical evaluations, history of antibiotic use, and the presence of the organism and/or toxins A & B (i.e., TcdA and TcdB, respectively) in the stool. Enzyme-linked immunoassay (EIA) tests are the most frequently used test format for measuring toxin in the stool specimens, with tissue culture combined with specific neutralization being the gold standard for detecting stool toxin. More recently, polymerase chain reaction (PCR) tests are available for determining the presence of *C. difficile* toxin A and B genes (tcdA and tcdB) and these are used as stand-alone tests and in combination with the detection of glutamate dehydrogenase (GDH) for ruling out *C. difficile*-negative patients. All of these assays are suitable for detecting the presence of *C. difficile* as an aid to diagnosis but do not provide information about the severity of disease or confirming that *C. difficile* actually is responsible for symptoms in patients with inflammatory bowel disease (IBD), irritable bowel syndrome (IBS), other enteric infections and diarrhea causing agents like laxatives and antibiotics.

The presence and severity of the disease is an important factor for recommending a proper course of treatment. In general, patients with *C. difficile* disease often present with fever, have slightly raised white blood cells (leukocytosis), and experience mild abdominal pain. Carrier status includes those patients that are colonized with *C. difficile* but lack stool toxin and intestinal inflammation indicating that something else is causing the symptoms. Patients that are determined to be carriers may still be placed in isolation wards but wouldn't receive treatment for CDI. Determining carrier status is important when deciding on a course of treatment since antibiotics could actually disrupt the normal flora making the patient susceptible to *C. difficile* disease. In addition, a low level of cells as indicated by low levels of *C. difficile* GDH may further differentiate between patients that are infectious versus noninfectious and, thus, allowing discharge from isolation wards.

For patients with disease, mild cases respond well to stopping the inciting antibiotic while moderate to severe *C. difficile* disease cases often require antibiotic intervention. Currently, no single lab parameter is routinely used to stratify patients based on severity of *C. difficile*-associated disease (CDAD) for optimizing medical and/or surgical treatment. The relapse rate is about 20% of patients occurring within days to a month following the end of antibiotic treatment.

BRIEF DESCRIPTION OF SEVERAL VIEWS OF THE DRAWINGS

Illustrative embodiments of the invention are described in detail below with reference to the attached drawing figures, wherein:

FIG. 4A depicts a summary of biomarker results for patients with a clinical cure (no symptoms and no *C. difficile* during and/or after initial treatment) according to embodiments of the invention;

FIG. 4B depicts a summary of biomarker results for patients with bacterial reinfection (return of *C. difficile* in absence of symptoms during and/or after initial treatment) according to embodiments of the invention;

FIG. 4C depicts a summary of biomarker results for patients with clinical recurrence or no cure (return of symptoms and *C. difficile* during and/or after initial treatment) according to embodiments of the invention;

FIG. 7 depicts a summary of monitoring a patient cured of *C. difficile* using Dificid antibiotic treatment with biomarkers of *C. difficile* disease including mean GDH (ng/mL), toxin (Optical Density by ABII ELISA), and lactoferrin levels (μg/mL) according to embodiments of the invention;

FIG. 8 depicts a summary of monitoring a patient having continued infection with *C. difficile* during Rifaximin antibiotic treatment using biomarkers of *C. difficile* disease including mean GDH (ng/mL), toxin (Optical Density by ABII ELISA), and lactoferrin levels (μg/mL) according to embodiments of the invention; and FIG. 9 depicts the utilization of a diagnostic biomarker panel including quantitative GDH, quantitative lactoferrin, and stool toxin as an aid in differentiating patients with *C. difficile* disease from those with carrier status.

DETAILED DESCRIPTION

Figures 1A, 1B:
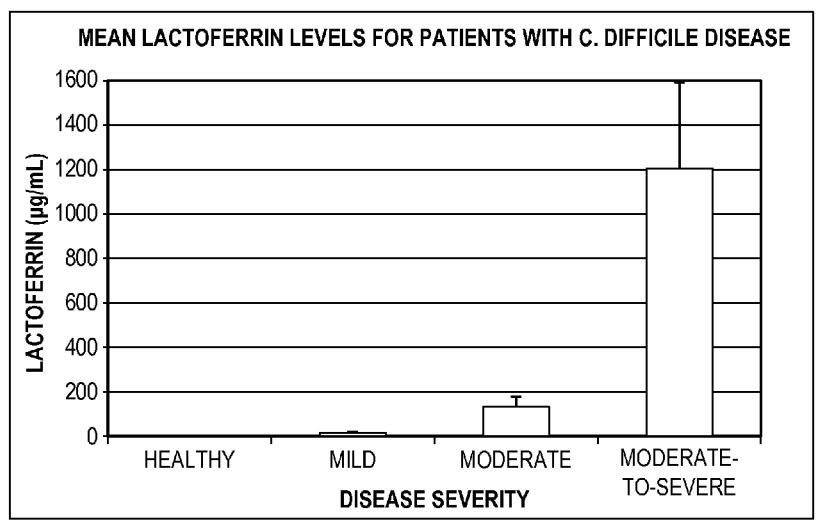
FIG. 1A depicts patient characteristics for patients diagnosed with *C. difficile* disease according to embodiments of the invention.
FIG. 1B depicts mean lactoferrin levels (μg/mL±standard error) for patients with clinically defined cases of *C. difficile* disease stratified by severity according to embodiments of the invention.

The present invention is directed to test methods for aiding in stratifying patients based on severity of *C. difficile* disease. Stratifying patients with disease based on severity using a panel of biomarkers is a new concept that is critically needed because of the increase in incidence and frequent severe presentations and overuse of antibiotics. The emergence of the outbreak strain ribotype ARL 027 that produces more toxin and spores has been linked with more severe *C. difficile* disease and a greater chance of relapse. In addition, newer medications like the antibiotic fidaxomicin (Dificid) offer additional treatment options for *C. difficile* disease. In a study published by L. Kyne et al. 1999, the authors performed a detailed characterization of disease states for an outbreak of CDAD in Dublin, Ireland. This particular outbreak involved 14 patients that were stool cytotoxin positive but asymptomatic. Of the symptomatic patients, 25% had mild-self-limiting disease with no antibiotic treatment, 35% had moderately severe *C. difficile* disease responding to antibiotic treatment and 40% developed severe disease with prolonged symptoms lasting between eleven to thirty-six days. A total of 8% of the patients with *C. difficile* disease progressed to severe colitis with pseudomembranes and toxic megacolon. The authors noted that physicians should be aware of early indicators of disease severity in order to lower morbidity and mortality for cases of *C. difficile* disease.

A combination of clinical presentations and various lab parameters have been evaluated for stratifying patients by disease activity (e.g., mild, moderate, and moderate-to-severe). White blood cell count (WBC), serum albumin level (indicator of leakage into the bowel), and creatinine level for monitoring kidney failure are the most commonly used lab indicators for disease activity for *C. difficile*. Mild to moderate cases of *C. difficile* usually present with a WBC≤15,000/μL, normal serum creatinine (<2.0 mg/dL) and albumin levels (≥2.5 g/dL). Symptoms include having less than 10 watery stools without blood per day and mild cramping lasting for up to an average of 4 days. A common treatment for patients with an initial episode of mild to moderate *C. difficile* disease is treatment with a member of the nitroimidazole class of antibiotics. For example, mild to moderate *C. difficile* disease may be treated with 500 mg metronidazole, three times daily for ten days. Most cases resolve with no further complications, but up to 25% of these cases may relapse multiple times and require a second round of antibiotics, which historically has included treatment with a member of the glycopeptide class of antibiotics, such as vancomycin. However, now such second rounds of antibiotics include members of the macrocyclic class of antibiotics, such as fidaxomicin (Dificid).

Patients over the age of sixty-five with multiple co-morbidities are at a higher risk for *C. difficile* disease and more often suffer from more severe disease leading to multiple relapses. Severe fulminant *C. difficile* disease is characterized by having eleven or more liquid stools per day for more than ten days. Stool specimens often contain mucus and may be bloody. Defined lab parameters for fulminant *C. difficile* colitis are WBC≥15,000/μL, a rising serum creatinine (50% increase and levels≥2.0 mg/dL) indicating poor kidney function and albumin levels dropping below 2.5 g/dL showing loss of protein because of exudation of serum into the bowel. Clinical presentations may involve pseudomembranes on endoscopy, severe abdominal pain and cramping, and colonic thickening observed by CT scan. Toxic megacolon stemming from ileus may occur causing nausea, vomiting, severe dehydration, and extreme lethargy. Treatment for severe and relapsing cases of *C. difficile* disease usually involves 125 mg vancomycin 4 times per day for 10 days.

Identifying disease activity for patients with *C. difficile* infection is imperative for proper treatment and better outcome with decreased morbidity and mortality. An embodiment of the invention provides a diagnostic parameter for assessing severity in *C. difficile* disease by measuring fecal lactoferrin and using the measurement of fecal lactoferrin as an indicator for intestinal inflammation caused by *C. difficile*. Additional embodiments are directed towards the measurement of biomarkers of disease in patients infected with *C. difficile* for monitoring the effectiveness of treatment and potential for relapse, as will be discussed in further detail below.

*C. difficile* disease is an inflammatory disease involving the infiltration of activated neutrophils across the mucosa into the lumen causing colitis and in severe cases, the formation of pseudomembranes. Human lactoferrin is a glycoprotein that is present in most mucosal secretions and a primary component of the granules of activated neutrophils. During the onset of intestinal inflammation from *C. difficile*, activated neutrophils infiltrate the intestinal lumen causing an increase in fecal lactoferrin.

Fecal specimens are routinely collected for C. difficile testing (antigen and toxin). Accordingly, additional testing can be done to measure the level of fecal lactoferrin for determining the amount of intestinal inflammation as an indicator of disease severity. In addition, combining the presence of antigen and the levels of toxins A and B with fecal lactoferrin concentrations can help the physician in determining if a patient is a carrier from patients that have true mild to severe infections for optimal medical treatment.

In an embodiment of the present invention, a method for assessing disease severity in patients with *C. difficile* disease using fecal lactoferrin levels is provided. Toxin A is a strong chemotactic protein that causes the release of IL-8 and the infiltration of activated neutrophils into the intestinal mucosa. In fact, toxin A concentrations of 100-fold less than that of toxin B have been shown to stimulate the release of IL-8. Toxin A also stimulates other pro-inflammatory cytokines including Il-1β and tumor necrosis factor alpha (TNF-α). Toxin B is a cytotoxin that causes tissue damage and inflammation that contributes, along with toxin A that causes fluid accumulation, to disease. The combined effects of the enterotoxic and chemotactic toxin A and cytotoxic effects of toxin B strongly contribute to the severity of disease. In a study by Kuehne et al., knockout mutants showed that both A+B− and A−B+ mutants were cytotoxic and caused disease in the hamster model. An interesting finding was that when tcdB was inactivated by an insertion, the resulting A+B− mutant showed increased cytotoxicity of toxin A in cell culture. The increased cytotoxicity was not neutralized completely by anti-toxin A specific antibody. The reason for the increase of cytotoxicity following the inactivation of tcdB was not determined but thought to be due to increased expression. The double knockout mutant A−B− did not cause disease in the hamster. These results confirmed that both TcdA and TcdB in combination and independently cause disease. In another study, the analysis of A−B+ isolates showed a variant toxin B that was significantly more lethal in a mouse than normal toxin B. These studies support the role of both toxins in the disease. A method for determining the presence of intestinal inflammation in combination with the presence of toxin in stool can offer additional information on disease status for patients with *C. difficile* infection.

An embodiment of the present invention provides for determining the presence of *C. difficile* disease using a biomarker panel that includes, by way of example, *C. difficile* antigen (GDH), toxins A (tcdA or TcdA) and B (tcdB or TcdB) for determining the presence of toxigenic *C. difficile*. As will be understood, further embodiments of the invention utilize additional biomarkers for *C. difficile* infection. When a diagnosis of *C. difficile* disease is concluded, fecal lactoferrin concentrations may be used to determine disease severity. In patients suspected of infection with *C. difficile*, if GDH is present, indicating the presence of *C. difficile*, then toxins A and/or B (genes and/or protein) are detected to show the presence of toxigenic *C. difficile* followed by measuring fecal lactoferrin levels as an indicator of intestinal inflammation. Knowing whether toxigenic *C. difficile* is present in combination with a lactoferrin concentration will help to determine disease severity to optimize treatment.

In embodiments, serial measurements of biomarkers for *C. difficile* infection are utilized. For example, lactoferrin, GDH, toxin A, and/or toxin B levels may be monitored at regular intervals during analysis and/or treatment to monitor disease status and/or treatment effectiveness. In embodiments, serial analysis of the presence of one or more biomarkers (e.g. GDH, toxins A and/or B) provides an indicator of the bacteria, which may be used to determine a patient's response to treatment. Most antibiotic treatments are administered for ten (10) days followed by a clinical assessment for cure. In addition, following the 10-day regiment of antibiotics, some patients remain a carrier for *C. difficile* leaving them at risk of a clinical relapse. Information on the effectiveness of treatment within days of the initial episode may allow for adjustment in drug therapy resulting in optimal medical management of patients. For instance, patients that are infected with the outbreak strain, ribotype 027 that produces more toxin, are at a higher risk for sever disease leading to colectomy and/or death. These patients would benefit from close monitoring of their *C. difficile* disease using biomarkers of inflammation and for the amount of *C. difficile* and its toxins. By identifying patients that aren't responding to treatment earlier in their 10-day regiment may offer the option to switch the therapy for improved outcome.

In embodiments, the level of lactoferrin in fecal samples provides an indication of the severity of *C. difficile*. For example, "mild" *C. difficile* disease may be indicated in samples with lactoferrin levels close to 7.25 µg/mL lactoferrin. In embodiments, a diagnosis of mild *C. difficile* disease is indicated in samples with lower lactoferrin levels combined with clinical indicators for defining the mild disease. For example, clinical indicators such as the number of unformed stools per day, a presence of fever, abdominal pain, and vomiting may be characterized and/or determined as being indicative of a diagnosis of mild *C. difficile* disease, and may be analyzed together with a low measurement of lactoferrin near or around baseline levels (<7.25 µg/mL lactoferrin), to determine disease severity. In embodiments, clinical indicators for a diagnosis of mild *C. difficile* include having three to five stools per day and a white blood cell count less than or equal to 15,000/mm$^3$. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with mild *C. difficile*.

In another example, "moderate" *C. difficile* disease may be indicated in samples with levels more than 99.99 µg/mL lactoferrin. In some embodiments, a diagnosis of moderate *C. difficile* disease is indicated in samples with more than 99.99 µg/mL lactoferrin, combined with clinical indicators for defining the moderate disease. For example, clinical indicators such as the number of unformed stools per day, a presence of fever, abdominal pain, and vomiting may be characterized and/or determined as being indicative of a diagnosis of moderate *C. difficile* disease, and may be analyzed together with a measurement more than 99.99 µg/mL lactoferrin, to determine disease severity. In embodiments, clinical indicators for a diagnosis of moderate *C. difficile* include having six to nine stools per day, a white blood cell count from 15,001/mm$^3$ to 20,000/mm$^3$, and moderate abdominal pain. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with moderate *C. difficile*.

In a further example, "moderate-to-severe" *C. difficile* disease may be indicated in samples close to 500 µg/mL or greater lactoferrin. In some embodiments, a diagnosis of moderate-to-severe *C. difficile* disease is indicated in samples close to 500 µg/mL or greater lactoferrin, combined with clinical indicators for defining the moderate-to-severe disease. For example, clinical indicators such as the number of unformed stools per day, a presence of fever, abdominal pain, and vomiting may be characterized and/or determined as being indicative of a diagnosis of moderate-to-severe *C. difficile* disease, and may be analyzed together with a measurement close to 500 µg/mL or greater lactoferrin, to determine disease severity. In embodiments, clinical indicators for a diagnosis of moderate-to-severe *C. difficile* include having ten or greater stools per day, a white blood cell count of 20,001/mm$^3$ or greater, and severe abdominal pain. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with moderate-to-severe *C. difficile*.

One exemplary method of testing for the presence of the *C. difficile* GDH biomarker is to use the C. DIFF CHEK™-60 test, which uses antibodies specific for *C. difficile* GDH. The Microassay Plate contains immobilized polyclonal antibody against the GDH antigen, while the Conjugate consists of a highly specific monoclonal antibody conjugated to horseradish peroxide. If the GDH antigen is present in the specimen, a color is detected due to the enzyme-antibody-antigen complexes that form in the assay.

One exemplary method of testing for the presence of toxin A and toxin B is to use the *C. DIFFICILE* TOX A/B II™ test, which uses antibodies to *C. difficile* toxins A and B. The test utilizes immobilized affinity-purified polyclonal antibody against toxins A and B, and the detecting antibody consists of a mixture of toxin A monoclonal antibody conjugated to horseradish peroxidase and toxin B polyclonal antibody conjugated to horseradish peroxidase. If toxins A and B are present in the specimen, a color is detected due to the enzyme-antibody-antigen complexes that form in the assay.

One exemplary method of testing for the presence of GDH, toxin A and toxin B is to use the QUIK CHEK COMPLETE™ test, which uses antibodies specific for GDH and toxins A and B of *C. difficile*. The device contains three vertical lines of immobilized antibodies, the antigen test line contains antibodies against *C. difficile* GDH, and the control line is a dotted line that contains anti-horseradish peroxidase antibodies. The toxins A and B test line contains antibodies against *C. difficile* toxins A and B and the Conjugate consists of antibodies to GDH and antibodies to toxins A and B coupled to horseradish peroxidase. The GDH reaction is examined visually for the appearance of a vertical blue line, which indicates a positive test, while a blue line also indicates a positive test for toxin A and toxin B.

One exemplary method of testing for the presence of *C. difficile* toxin is the C. DIFFICILE TOX-B TEST™, which uses a tissue culture format to detect the presence of cytotoxic activity in fecal specimens and confirms the identification of *C. difficile* toxin using specific antitoxin. The test confirms the presence of *C. difficile* toxin by neutralizing the cytotoxic activity with a reagent that is a specific antitoxin. In the assay, if *C. difficile* toxin is present, the cells in the well with PBS will become round, demonstrating the presence of the cytotoxic activity, while the presence of *C. difficile* toxin is confirmed if the cytotoxic activity is neutralized in the well containing antitoxin.

One exemplary method of treating *C. difficile* is through a native flora transplant. This process, also referred to as Fecal (or Faecal) Microbiota Transplantation (FMT), is the restoration of the colonic flora by introducing healthy bacterial flora through infusion of stool, e.g. by enema, obtained from a healthy human donor. A native flora transplant can also be administered as a liquid that the patient drinks.

The following are examples of procedures which have been utilized to establish the preferred assays according to the present invention. The following examples are merely exemplary and not presented by way of limitation.

EXAMPLE 1

Fecal lactoferrin levels were evaluated in patients with clinically defined *C. difficile* disease ranging from mild to moderate-to-severe disease. Briefly, patients with clinically confirmed *C. difficile* disease presenting with a spectrum of severity were recruited along with fourteen age-sex matched healthy subjects defined as having no intestinal illnesses. Disease activity was defined by physician's assessment and based on symptoms, serum albumin, WBC counts and co-morbidities. Fecal lactoferrin was measured using a quantitative enzyme immunoassay (EIA). *C. difficile* glutamate dehydrogenase (GDH) and toxins A and B in stool were detected using a membrane-based EIA. Toxigenic culture was done using spore enrichment and both isolates and stool specimens were tested by tissue culture assay for cytotoxicity.

Results

Thirty-nine clinically confirmed cases of *C. difficile* disease (fifteen moderate-to-severe, twenty-one moderate and three mild) were tested during a six month period. Ages ranged from thirty-two to eighty-nine years and fifty percent were female. The predominant co-morbidities were diabetes (31%), cancer (23%) and renal failure (23%). All patients were GDH-positive and toxigenic *C. difficile* was isolated from all but four patients. The mean lactoferrin levels (μg/mL±std error) were 1198±404 for moderate-to-severe, 132±50 for moderate, 12±5 for mild and 2±0.3 for healthy subjects. Stool toxin was detected by tissue culture in 87% ($^{13}/_{15}$) of moderate-to-severe, 71% ($^{15}/_{21}$) of moderate and 33% ($^{1}/_{3}$) for mild disease. Two of the moderate-to-severe patients with the lowest lactoferrin levels (≤8 μg/mL) and three of the four lowest with moderate (≤12 μg/mL) were also tissue culture-negative. Of these patients, both of the severe and two of the four moderate patients had negative stool cultures. All of these patients had co-morbidities that contributed to the clinical assessments. Our conclusion is that in a clinical setting, co-morbidities can complicate the clinical assessment for *C. difficile* infection. Our results show that fecal lactoferrin is useful for indicating disease severity in patients with *C. difficile* infection.

Accordingly, FIG. 1A details the patient characteristics for clinically confirmed cases of *C. difficile* disease. Most patients were >64 years old, experienced pain, had liquid stools and suffered with co-morbidities including diabetes, cancer, renal failure and pneumonia. FIG. 1B shows that lactoferrin levels were significantly higher between mild, moderate, and moderate-to-severe cases of *C. difficile* disease, and trended higher for the moderate-to-severe group.

Figure 2:
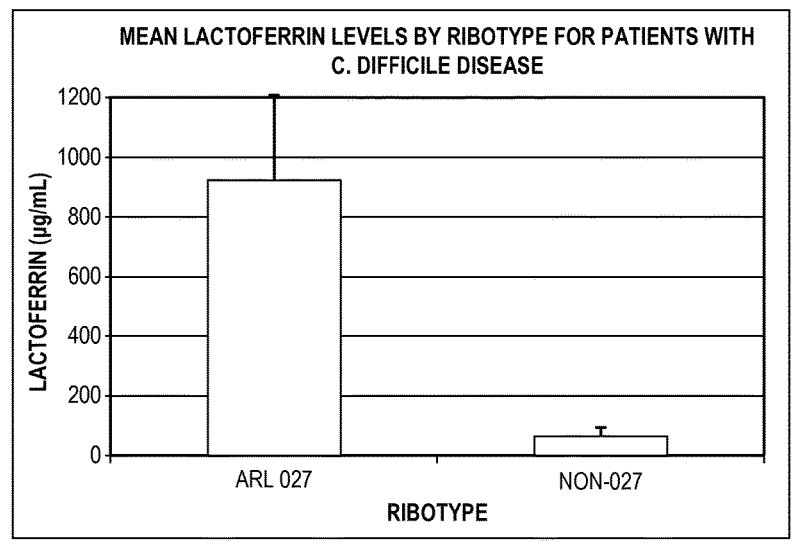
FIG. 2 depicts mean lactoferrin levels (μg/mL±standard error) for patients stratified by ARL 027 versus other ribotype *C. difficile* infections according to embodiments of the invention.

FIG. 2 shows the mean lactoferrin levels for patients with clinically confirmed *C. difficile* disease grouped by ribotype. Patients infected with ARL 027 had significantly higher levels of lactoferrin than patients infected with other ribotypes. Studies have shown that patients infected with ARL 027 tend to have stool toxin and present with more severe disease.

EXAMPLE 2

Fecal *C. difficile* GDH, toxins A and B, and human lactoferrin levels were measured in several subjects with *C. difficile* disease during antibiotic treatment. Both subjects with clinically confirmed *C. difficile* disease were monitored for the presence of GDH, toxins A and B and fecal lactoferrin by enzyme-linked immunoassay (EIA). Specimen collection was initiated at the start of antibiotic treatment and was continued on a daily to weekly basis when possible. A symptom log was kept by each patient and all treatments were recorded during the test period. Both patients showed a rapid response to antibiotic treatment with fecal GDH, toxins A and B, and fecal lactoferrin reaching baseline within 24 hours. Antigen, toxin and fecal lactoferrin remained negative during the antibiotic therapy. Following the treatment, both patients experienced a clinical relapse and showed a rapid increase for all parameters. Following a second course of antibiotics, all parameters returned to baseline. At completion of the second course of antibiotics, all parameters increased rapidly in absence of clinical symptoms. Both GDH and toxin remained present for 3 to 4 weeks but fecal lactoferrin quickly returned to baseline. No antibiotics were administered since there were no clinical symptoms and patients remained healthy.

Results

In this evaluation, it was observed that *C. difficile* GDH, toxin and fecal lactoferrin levels responded quickly to antibiotic therapy by returning to baseline (negative). More interestingly, both GDH and toxin were present without clinical symptoms and with no intestinal inflammation as determined by baseline lactoferrin. These results show a role for fecal lactoferrin in combination with antigen and toxin measurements for determining which cases of *C. difficile* disease may require no further treatment with antibiotics. In addition, our invention provides a role for fecal lactoferrin in monitoring *C. difficile* disease. By determining the amount of intestinal inflammation using lactoferrin in *C. difficile* disease patients along with clinical assessments, the identification of patients for severity of disease may prove useful for optimizing treatment and leading to better patient outcomes.

Treatment may be optimized for *C. difficile* disease since varying levels of severity call for different treatment recommendations. For example, mild cases of *C. difficile* disease often receive no antibiotic treatment. In contrast, a case of moderate severity may call for an antibiotic such as metronidazole while a moderate-to-severe case of *C. difficile* disease may be treated with antibiotics such as vancomycin and fidaxomicin (Dificid).

Figure 3:
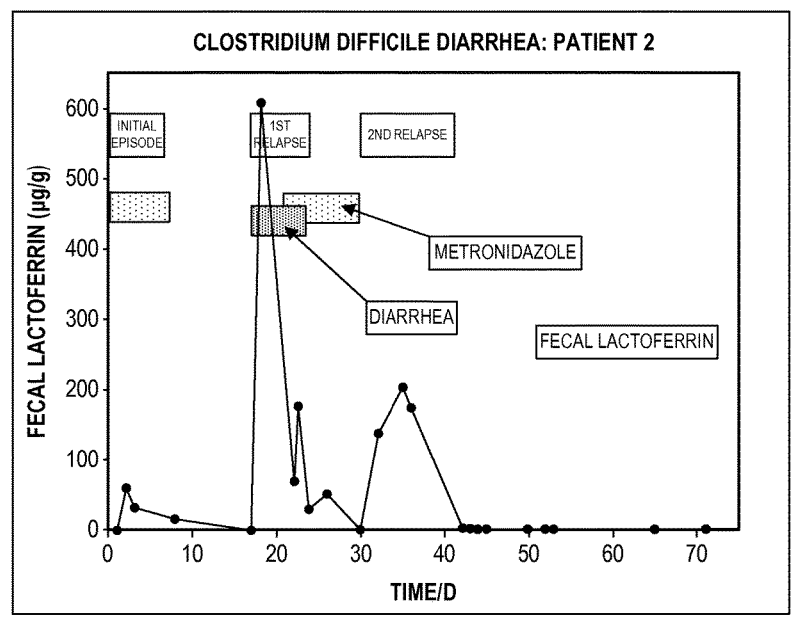
FIG. 3 depicts daily monitoring of lactoferrin levels during and after antibiotic treatment in a patient with *C. difficile* disease according to embodiments of the invention.

FIG. 3 illustrates daily lactoferrin levels from the initial episode of *C. difficile* infection, during, and after antibiotic treatment. Lactoferrin was elevated (≥7.25 µg/mL) during the initial episode and for both periods of relapse. Levels drop rapidly once treatment is started and increased as symptoms return.

EXAMPLE 3

Patients (pts) with diarrhea and positive stool toxin (TcdA and TcdB) and/or glutamate dehydrogenase (GDH) were recruited with Informed Consent. Stool specimens were collected starting at admission (T=0) to Follow-up (T=F). GDH, toxin, and lactoferrin (LF: median µg/g) were measured in stool specimens by immunoassay. Bacterial culture and counts (median CFU#/g) were done using ethanol enrichment and isolates were ribotyped. A total of 18 inpatients were recruited and followed for a median period of 21 days from T=0 to T=F. Median age was 75yr and the male:female ratio was 1:3.5. Pts were stratified into 3 groups (i) pts who were treated and showed no recurrence (N=9). (ii) pts who were treated with complete resolution of symptoms but had CDI (N=5) and (iii) pts that responded initially to treatment but relapsed (N=4).

Results

Patients in group (i) went from strongly positive for GDH, toxin and a spore count of $10^4$ at T=0 to negative for all biomarkers at T=F. LF fell from 406 to 4 during this period (Table 1a). Four of the 5 pts in group (ii) were positive for GDH, toxin, and had a spore count of $10^4$ at T=0. At T=F, 3 of the 5 pts were toxin negative, 3 pts remained GDH-positive and all pts had spores ($10^3$). LF for these pts dropped from 85 to 2 associated with resolution of symptoms (Table 1b). For group (iii), all 4 pts remained symptomatic and stayed strongly positive for GDH, toxin, and had a spore count of $10^4$. LF levels for this group were similar at both T=0 and T=F (362 and 315, respectively) (Table 1c). A total of 5 (28%) pts had 027 CDI at T=0. In group (ii), 3 of 5 pts were reinfected with 027 as carriers. In group (iii), 1 patient converted to 027. **All of the 027 isolates were fluoroquinolone resistant. In our study, at T=F 50% of pts had no CDI, 28% became carriers and 22% remained ill. GDH, toxin and LF levels all correlated with the presence of clinical disease. *C. difficile* continues to be a complex infection, and accurate diagnosis of disease relies on the clinical history used in conjunction with biomarkers for the organism and for inflammation.

FIG. 4A shows the results of CDI biomarkers before and after antibiotic treatment for *C. difficile* disease. All of the patients in this group had a clinical cure meaning no symptoms and no *C. difficile* detected during and after initial antibiotic treatment.

FIG. 4B shows the results of CDI biomarkers before and after antibiotic treatment for *C. difficile* disease. All patients in this group had a reinfection of *C. difficile* meaning that the *C. difficile* organism was detected in absence of symptoms during and/or after initial antibiotic treatment.

FIG. 4C shows the results of CDI biomarkers before and after antibiotic treatment for *C. difficile* disease. All patients in this group had a clinical recurrence or no cure meaning that symptoms and the *C. difficile* organism was maintained or returned during and/or after initial antibiotic treatment.

Figure 5:
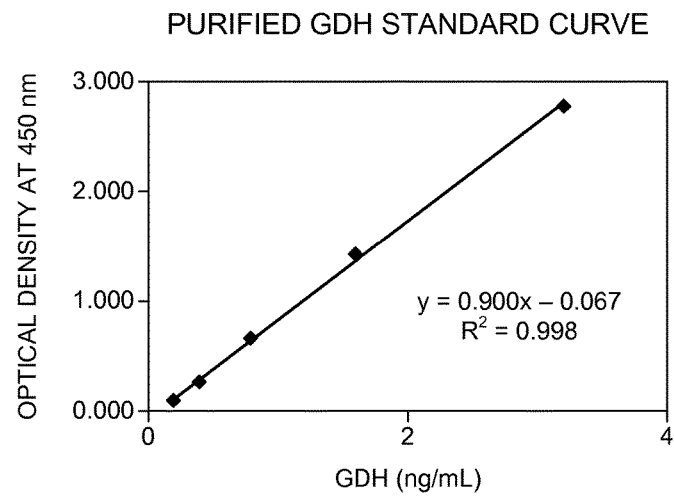
FIG. 5 depicts a standard curve generated by a quantitative GDH ELISA test using purified *C. difficile* GDH antigen according to embodiments of the invention.
Figure 6:
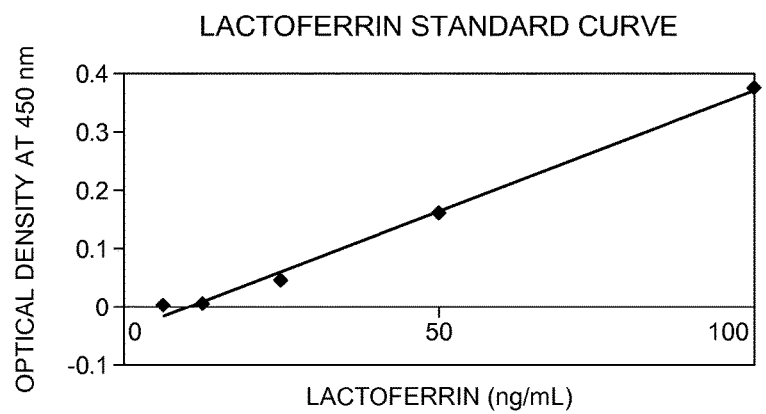
FIG. 6 depicts a standard curve generated by a quantitative lactoferrin ELISA test using purified lactoferrin antigen according to embodiments of the invention.

FIG. 5 depicts a standard curve generated by a quantitative GDH ELISA test using purified *C. difficile* GDH antigen while FIG. 6 illustrates a standard curve generated by a quantitative lactoferrin ELISA test using purified lactoferrin antigen.

FIG. 7 depicts the monitoring of a patient cured of *C. difficile* using Dificid antibiotic treatment with biomarkers of *C. difficile* disease including mean GDH (ng/mL), toxin (Optical Density by ABII ELISA), and lactoferrin levels (µg/mL). As illustrated in FIG. 7, fecal samples of the patient were tested and, as is evident, levels of GDH decreased and were not detected upon concluding the antibiotic regiment biomarkers show a cure in the patient on Dificid. Additionally, the levels of lactoferrin and toxin were also markedly decreased. This is useful when identifying whether or not a treatment therapy is effective.

FIG. 8 depicts the monitoring of a patient having continued infection with *C. difficile* during Rifaximin antibiotic treatment using biomarkers of *C. difficile* disease including mean GDH (ng/mL), toxin (Optical Density by ABII ELISA), and lactoferrin levels (µg/mL). In contrast to FIG. 7, FIG. 8 illustrates that fecal samples from the individual still suffering from *C. difficile* disease experienced an increase in GDH. Specifically, the level of GDH appears to decrease but then begins to rise as the therapy proves to be ineffective.

FIG. 9 depicts the utilization of a diagnostic biomarker panel including quantitative GDH, quantitative lactoferrin and stool toxin as an aid in differentiating patients with *C. difficile* disease from those with carrier status. The results show the levels of biomarkers for differentiating patients with carrier status from those with active disease. A combination of the biomarkers and clinical symptoms are used in combination to determine carriers from patients with disease. For example, patients with lactoferrin levels close to baseline (7.25 µg/g), GDH<1000 ng/g, and no or low toxin are suspected of carrier status. In contrast, patients with stool toxin, higher lactoferrin and GDH levels are suspected of disease. The molecular assays like PCR are highly sensitive and show positive results for patients with carrier status and disease. The addition of biomarkers with clinical assessments offer a method for determining which patients require treatment for optimal outcome.

In an alternative embodiment, fecal calprotectin may be utilized rather than, or in addition to, fecal lactoferrin as a non-invasive marker for measuring intestinal inflammation. For example, in a person diagnosed with *C. difficile* disease, a quantitative level of fecal calprotectin may be measured and the quantitative level may be associated with a disease severity including mild, moderate, and moderate-to-severe. Further, fecal calprotectin may be measured subsequent to treatment to monitor a person's response to medical treatment or an activity level of the disease.

In summary, the present invention is directed to non-invasive methods for identifying a severity of C. difficile disease in persons diagnosed with C. difficile disease using lactoferrin. The identified disease severity may be used to recommend a preferred course of treatment for the person. The present invention is further directed to utilizing changes in lactoferrin levels to monitor a person's disease activity and/or response to treatment.

The immunoassays of the present invention detect lactoferrin, a stable protein that serves as an indicator of intestinal inflammation, and provide quantitative fecal lactoferrin levels for associating a disease severity to C. difficile disease and for monitoring disease activity. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects herein above set forth together with other advantages which are obvious and which are inherent to the method. It will be understood that certain features and subcombinations are of utility and may be employed without reference to other features and subcombinations. This is contemplated by and is within the scope of the claims.

What the invention claimed is:

1. A method of measuring a quantity of C. difficile in a fecal sample, the method comprising:
obtaining a fecal sample from a patient infected with C. difficile;
diluting the fecal sample;
quantitatively measuring a level of C. difficile glutamate dehydrogenase (GDH) in the fecal sample, wherein a level of C. difficile GDH<1000 ng/g comprises a low level of C. difficile GDH, and wherein a level of C. difficile GDH>or equal to 1000 ng/g comprises a high level of C. difficile GDH;
determining that the patient has a low subclinical quantity of C. difficile indicating a carrier status when the fecal sample has the low level of C. difficile GDH, and withholding antibiotic treatment from the patient determined to have the low subclinical quantity of C. difficile indicating the carrier status; and
determining that the patient has active C. difficile disease when the fecal sample has the high level of C. difficile GDH, and treating the patient determined to have active C. difficile disease with antibiotics.

2. The method of claim 1, further comprising determining a level of toxin A or toxin B in the fecal sample.

3. The method of claim 1, further comprising determining a level of lactoferrin in the fecal sample to identify patients with intestinal inflammation.

4. The method of claim 1, further comprising determining a level of one or more other antigens in the fecal sample, wherein the one or more other antigens are quantitatively measured.

5. The method of claim 1, further comprising contacting the fecal sample with immobilized polyclonal or monoclonal antibodies to C. difficile GDH to create an antibody bound sample.

6. The method of claim 5, further comprising contacting the antibody bound sample with enzyme-linked polyclonal or monoclonal antibodies such that the enzyme-linked polyclonal or monoclonal antibodies are allowed to bind to capture C. difficile GDH and create an enzyme-linked antibody bound sample.

7. The method of claim 6, further comprising adding a substrate to the enzyme-linked antibody bound sample for color development to create a readable enzyme-linked antibody bound sample.

8. The method of claim 7, further comprising determining an optical density of said readable enzyme-linked antibody bound sample using a wavelength, wherein the optical density corresponds to a level of C. difficile GDH in the readable enzyme-linked antibody bound sample.

9. The method of claim 8, wherein if said optical density of said readable enzyme-linked antibody bound sample is positive, said fecal sample contains the high level of C. difficile GDH.

10. The method of claim 1, further comprising determining a presence of toxin A or toxin B in the fecal sample, and determining a level of lactoferrin in the fecal sample.

11. The method of claim 10, wherein the withholding antibiotic treatment from the patient determined to have the low subclinical quantity of C. difficile indicating the carrier status comprises withholding antibiotic treatment from the patient when the fecal sample has the low subclinical quantity of C. difficile, and the level of lactoferrin in the fecal sample is about 7.25 µg/ng or less, and no toxin A or toxin B is present in the fecal sample.

12. The method of claim 10, wherein the determining that the patient has active C. difficile disease when the fecal sample has the high level of C. difficile GDH comprises determining that the patient has active C. difficile disease when the fecal sample has the high level of C. difficile GDH, the level of lactoferrin in the fecal sample is greater than 7.25 µg/ng, and toxin A or toxin B is present in the fecal sample.

* * * * *